(12) United States Patent
Hitzenberger et al.

(10) Patent No.: US 6,307,634 B2
(45) Date of Patent: *Oct. 23, 2001

(54) METHOD AND APPARATUS FOR RECORDING THREE-DIMENSIONAL DISTRIBUTION OF LIGHT BACKSCATTERING POTENTIAL IN TRANSPARENT AND SEMI-TRANSPARENT STRUCTURES

(75) Inventors: Christoph Hitzenberger; Angela Baumgartner, both of Vienna (AT)

(73) Assignee: Laser Diagnostic Technologies, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/755,917

(22) Filed: Jan. 6, 2001

Related U.S. Application Data

(60) Continuation of application No. 09/626,056, filed on Jul. 26, 2000, which is a division of application No. 09/079,495, filed on May 15, 1998, now Pat. No. 6,137,585.

(51) Int. Cl.[7] .................................................... G01B 9/02

(52) U.S. Cl. ......................... 356/484; 356/491; 356/497

(58) Field of Search .................. 356/484–485, 356/487

(56) References Cited

U.S. PATENT DOCUMENTS

| | | | |
|---|---|---|---|
| 4,735,476 | 4/1988 | Heffner et al. | 350/96.13 |
| 5,565,986 | 10/1996 | Knittel | 356/346 |
| 5,682,240 | 10/1997 | Redlitz | 356/349 |
| 6,137,585 | 10/2000 | Hitzenberger et al. | 356/484 |

OTHER PUBLICATIONS

Publication: "Ophthalmic Interferometry", Fercher. pp. 221–228. Optics In Medicine, 1993.

Publication: "Eye Length Measurement by Laser Doppler Interferometry (LDI)". Hitzenberger et al. Satellite Conference to the 15th International Congress of the International Commission for Optics (ICO–15 SAT). pp. 232–235. Germany, Aug. 1990.

Publication: "Ophthalmic Laser Interferometry". Fercher et al. Conference on Optical Instrumentation for Biomedical Laser Applications. Austria. Apr., 1986.

Publication: "Measurement of the Axial Eye Length and Retinal Thickness by Laser Doppler Interferometry (LDI)". Hitzenberger et al. Ophthalmic Technologies. SPIE vol. 1423, pp. 46–50. 1991.

Publication: "Optical Coherence Tomography". Huang et al. Science, vol. 254. Nov., 1991.

*Primary Examiner*—Frank G. Font
*Assistant Examiner*—Phil Natividad
(74) *Attorney, Agent, or Firm*—John L. Rogitz

(57) ABSTRACT

An apparatus is disclosed for generating data representative of a three-dimensional distribution of the light backscattering potential of a transparent or semi-transparent object such as a human eye. The apparatus includes an interferometer, both the reference beam and measurement beam of which are directed toward the object and reflected by respective reference and measurement sites thereof, such that axial motion of the object during measurement affects both beams equally. The measurement beam is raster scanned transversely across each measurement site for which data is obtained. Also, the frequency of one of the beams is shifted by a non-moving frequency shifter, such that the reflected beams combine and are modulated by a heterodyne heat frequency, which is detected when the object path difference is matched with the interferometer path difference. Because the non-moving frequency shifter can effectively generate a beat frequency of about 40 MHz, relatively rapid transverse and longitudinal scanning are facilitated.

40 Claims, 3 Drawing Sheets

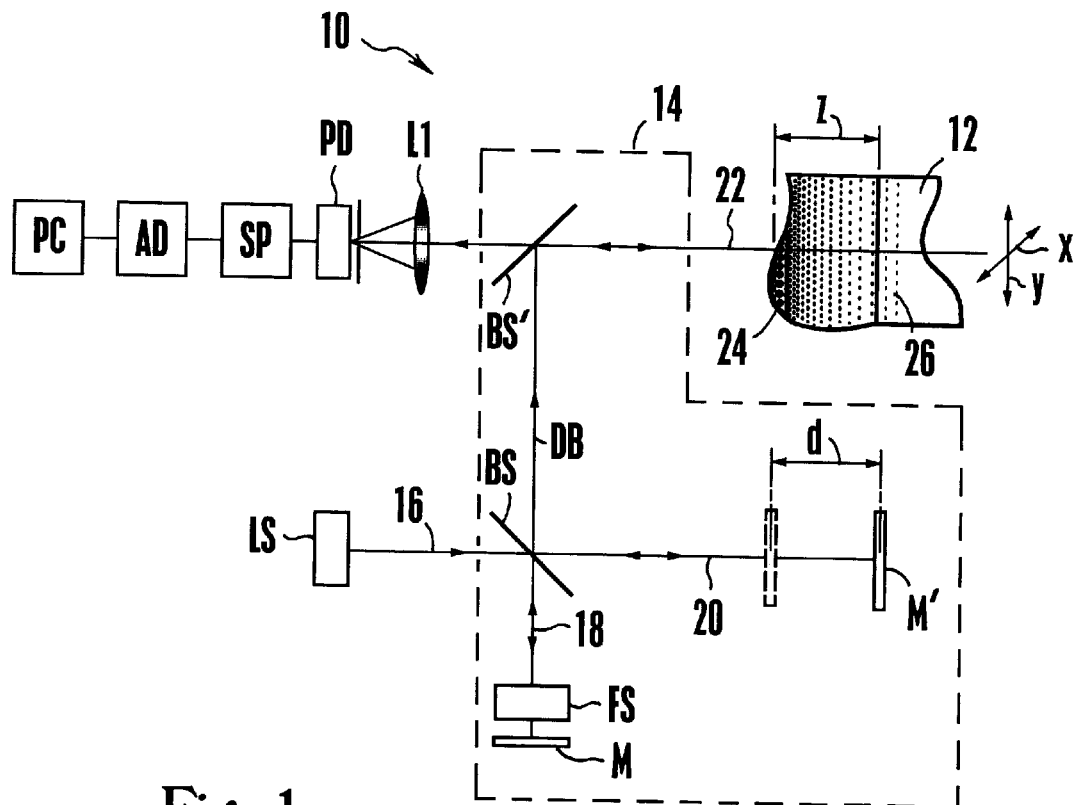
Fig. 1
Fig. 3
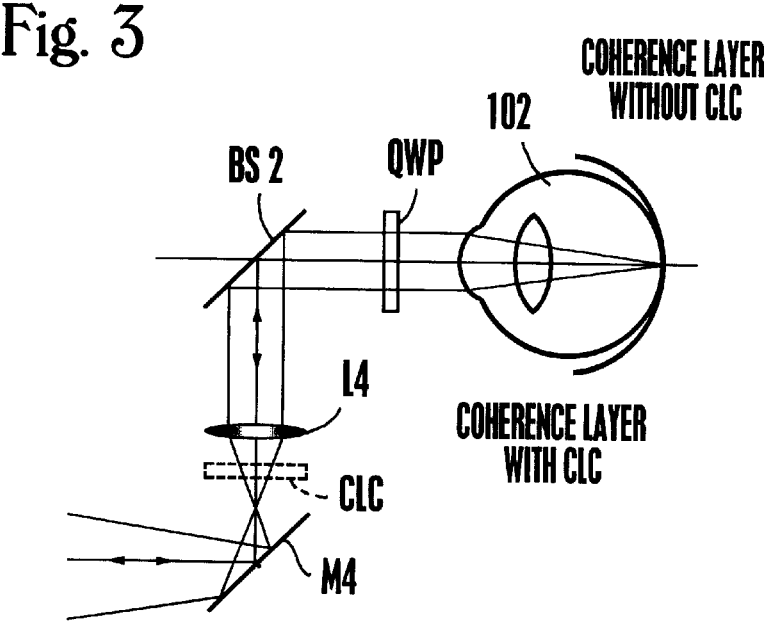

METHOD AND APPARATUS FOR RECORDING THREE-DIMENSIONAL DISTRIBUTION OF LIGHT BACKSCATTERING POTENTIAL IN TRANSPARENT AND SEMI-TRANSPARENT STRUCTURES

This application is a continuation of pending prior application Ser. No. 09/626,056, filed Jul. 26, 2000, which is a divisional of U.S. patent application Ser. No. 09/079,495, filed May 15, 1998, now U.S. Pat. No. 6,137,585. Priority from both of these applications is claimed.

FIELD OF THE INVENTION

The present invention relates generally to determining light backscattering at various depths in transparent and semi-transparent structures, and more particularly to methods and apparatus for diagnosing human eye conditions by detecting the reflection of light from various layers in the eye.

BACKGROUND

Detailed structural knowledge of transparent and semi-transparent objects can be gained by measuring the reflective backscattering of light from various layers in the objects. Such structural knowledge can be useful in various industrial applications such as semiconductor chip fabrication. Furthermore, knowing the precise structure of the eye of a human patient is useful in diagnosing certain conditions of the eye, including, for example, glaucoma.

German Patent No. 3201801A1 to Fercher discloses a method referred to as partial coherence interferometry ("PCI") in which light having a short coherence length is combined with a Michelson interferometer to locate the positions of reflecting surfaces within an object. In PCI, a measurement light beam from the interferometer is directed against a particular reflecting surface in the object, and a reference light beam is directed against a known reference surface. The position of the reflecting surface in the object is determined by matching the length of the known reference path that is traversed by the reference light beam to the unknown object path length that is traversed by the measurement light beam.

The above discussed PCI method results in the generation of so-called optical A-scans, which can be thought of as plots of backscattered light intensity as a function of depth within the object. U.S. Pat. No. 5,321,501, incorporated herein by reference, discloses a technique referred to as optical coherence tomography ("OCT") in which several A-scans are combined to effectively map the depth of an object.

The invention disclosed in the '501 patent is embodied in the commercial OCT instrument sold by Humphrey Instruments/Carl Zeiss. Unfortunately, the Humphrey-Zeiss instrument permits measuring only longitudinal sections, not transverse sections, and furthermore it requires that the section geometry be defined a priori. The present invention understands that it is desirable to measure both longitudinal and transverse sections to thereby generate a three dimensional map of the object, and that it is also desirable that the section geometry not be defined a priori. Moreover, the present invention recognizes that because the reference surface of the Humphrey-Zeiss instrument is not part of the object to be measured, the precision of the instrument can be degraded by axial movement of the object during measurement.

In addition to the above-mentioned drawbacks, the present invention recognizes that the speed of measurement of prior instruments is relatively slow, and that prolonged measurement time has undesirable consequences, as set forth in the following discussion. As mentioned above, the object path length is matched with the reference path length in PCI applications, including OCT. This matching, when it occurs, is indicated by the presence of interference fringes caused by the interference of the return reference beam with the return measurement beam. In early PCI applications, the interference fringes were visually detected, which significantly lengthened the time required to gather the backscattering data at the various layer depths. Unfortunately, prolonged data gathering periods limits the resolution of the data when the object being analyzed moves. In the case of the human eye, microsaccidic eye movements tend to limit the resolution of the data.

Accordingly, to facilitate more rapid detection of interference fringes, Hitzenberger et al., in an article entitled "Eye Length Measurement by Laser Doppler Interferometry ("LDI")", Int'l Conf. on Optics within Life Sciences, Garmisch-Partenkirchen, 1990, propose detecting the fringes by heterodyning. Specifically, the Hitzenberger et al. article discloses moving a reference mirror at constant speed to cause a Doppler frequency shift in one of the beams, causing the generation of a detectable "beat" frequency when the reference beam and measurement beam interfere with each other as they return from the object being measured.

As recognized by the present invention, however, while Doppler-based heterodyne detection is an improvement over the visual detection method, the use of mechanically moving parts nevertheless limits the speed of measurement by limiting the magnitude of the induced frequency shift, which is proportional to the speed of the reference mirror. Additionally, the present invention recognizes that mechanically-based heterodyning techniques can induce a varying beat frequency, causing demodulation complications, and also requiring a relatively large filter bandwidth (used during demodulation) to account for the variations. The large filter bandwidth in turn reduces the signal to noise ratio of the instrument.

Accordingly, it is an object of the present invention to provide a method and apparatus for generating a map of a transparent or semi-transparent object. Another object of the present invention is to provide a method and apparatus for rapidly generating a map of a human eye. Still another object of the present invention is to provide a method and apparatus for rapidly generating a map of a human eye that is easy to use and cost-effective, and that is not degraded by axial motion of the eye during measurement.

SUMMARY OF THE INVENTION

An apparatus is disclosed for detecting the distribution of light backscattering potential in an object, such as a human eye. The apparatus includes an interferometer which emits plural preferably short coherence-length light beams, with at least one of the light beams being directable toward the object. The light beams are reflected by respective surfaces to establish respective reflected light beams. At least one non-moving frequency shifter is positioned in at least one path of the light beams, and a receiver receives the reflected beams and generates a signal representative thereof. As intended by the present invention, the signal is usable for determining light backscattering sites in the object.

In a preferred embodiment, the plural light beams include at least a reference beam directed at a reference surface defined by the object and a measurement beam directed at a measurement site defined by the object. With this structure, axial motion of the object relative the interferometer equally affects the reference beam and measurement beam.

As disclosed in detail below, the frequency shifter changes the frequency of light beams passing therethrough. The frequency shifter is selected from the group of frequency shifters including acousto-optic frequency shifters, and phase modulators.

Preferably, the interferometer defines a reference arm and a measurement arm, and a first difference is established between the lengths of the arms. The reference beam travels a reference distance relative to the object, the measurement beam travels a measurement distance relative to the object, and a second difference is established between the reference distance and measurement distance. At least one arm length can then be established such that the first difference bears a proportional relationship to the second difference, and a beat frequency is received by the receiver when the differences are substantially matched. In a particularly preferred embodiment the interferometer includes at least one translationally movable path delay unit to selectively establish the at least one arm length.

If desired, polarized light can be used. When polarized light is used, a polarizer can be positioned in the light entrance path of the interferometer, and a half wave plate can be positioned in the arm of the interferometer in which the frequency shifter is positioned. Also, a quarter wave plate can be positioned in the light exit path.

In addition to the above structure, at least one spatial filter can be disposed in at least one of the arms to improve the quality of a wave front of light passing therethrough. Still further, a scanning mirror is positioned in the measurement arm and is tiltable in at least one degree of freedom to selectively establish a direction of propagation of the measurement beam. A coherence layer correcting element is juxtaposed with the scanning mirror to alter a length of a path traversed by the measurement beam in proportion to an angle established between the measurement beam and its null direction, typically the direction of the reference beam.

In another aspect, an apparatus for matching an object path difference with an interferometer path difference and identifying the matching by heterodyne detection of a reference beam and a measurement beam includes means for shifting the frequency of at least one of the reference beam, and the measurement beam, by at least ten megaHertz. Thereby, a beat frequency is generated when the object path difference bears a predetermined relationship to an interferometer path difference.

In still another aspect, a method is disclosed for generating data representative of a three-dimensional distribution of the light backscattering potential of an object defining at least one reference surface and plural measurement sites. The method includes directing a reference beam from a reference arm of an interferometer against the reference surface, and also directing a measurement beam from a measurement arm of the interferometer against the measurement site. The method further includes shifting the frequency of at least one beam by at least ten megaHertz. Reflections of the beams from the surfaces are combined and detected.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a schematic diagram of a first embodiment of the present invention using a Michelson interferometer, showing the measurement mirror in a null position in phantom and showing the measurement mirror in a measurement position in solid lines;

FIG. 3 is a schematic diagram of an alternate embodiment of a portion of the apparatus shown in FIG. 2, showing a coherence layer correcting element and showing a coherence layer in solid lines as it would appear without the correcting element, and showing the coherence layer in dashed lines as it would appear with the correcting element;

DETAILED DESCRIPTION OF THE PREFERRED EMBODIMENT

Figure 2:
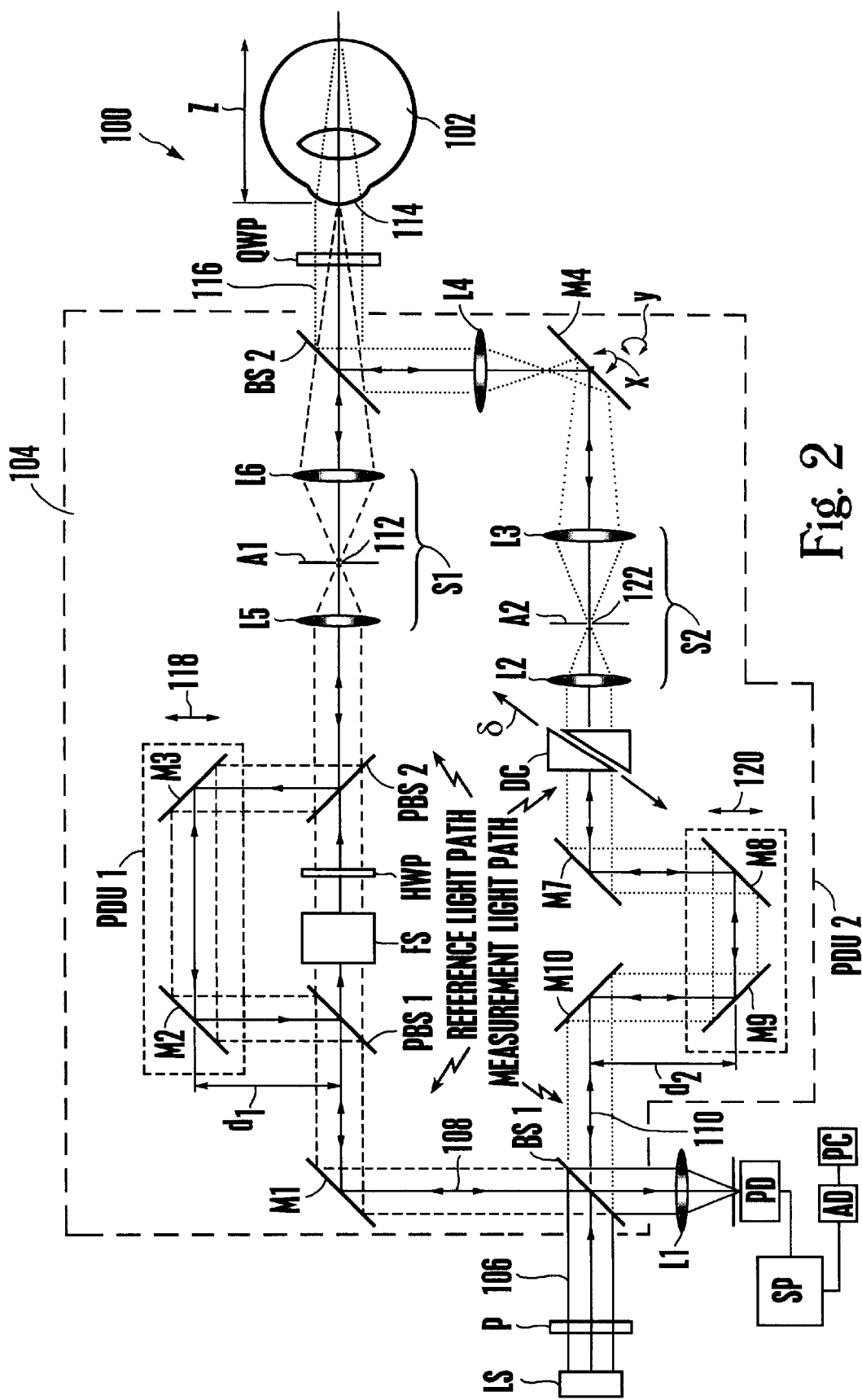
FIG. 2 is a schematic diagram of a second embodiment of the present invention using a modified Mach-Zehnder interferometer.

Referring initially to FIG. 1, an apparatus is shown, generally designated 10, for generating data representative of the three-dimensional distribution of light backscattering sites, and their respective reflectivities, in a transparent or semi-transparent object 12, such as a human eye. That is, the apparatus 10 measures the reflection of light by various sites within the object 12 along the longitudinal axis, i.e., z-axis, with the understanding that the z-axis is orthogonal to the transverse axes, i.e., the x and y axes. It is to be understood, however, that the apparatus 10 can be used to generate data representative of the three-dimensional distribution of light backscattering potential in objects other than eyes.

FIG. 1 shows a simplified embodiment that uses a Michelson interferometer 14. As shown, a short coherence, broadband light source LS directs a beam of light into an entrance path 16 of the interferometer 14. In the preferred embodiment, the light source LS includes a superluminescent diode and collimating optics. Light propagating along the entrance path 16 impinges upon an entrance beamsplitter BS, which splits the beam into a reference beam propagating along a reference arm or path 18 and a measurement beam propagating along a measurement arm or path 20. The reference beam is reflected by a reference mirror M back to the entrance beamsplitter BS, through which it propagates along a dual beam path DB to an exit beamsplitter BS'. Similarly, the measurement beam is reflected by a measurement mirror M' back to the entrance beamsplitter BS, which reflects the measurement beam to propagate along the dual beam path DB to the exit beamsplitter BS' such that the reference beam and the measurement beam form a coaxial dual beam.

To vary the length of the optical path through which at least the measurement beam propagates through the interferometer 14, at least the measurement mirror M' is translationally movable between a null position, indicated by dashed lines in FIG. 1, and plural measurement positions (only a single measurement position shown and indicated in solid lines in FIG. 1). When the measurement mirror M' is in the null position, the distance traversed by the measurement beam through the interferometer 14 is equal to the distance traversed by the reference beam through the interferometer 14. On the other hand, when the measurement mirror M' is in a measurement position that is distanced from the null position by an interferometer differential distance of "d", the distance traversed by the measurement beam through the interferometer 14 is equal to the distance traversed by the reference beam through the interferometer 14, plus two times "d". In this latter case, an interferometer optical path difference of magnitude "2d" is established between the distances traversed by the reference and measurement beams through the interferometer 14. It is to be understood that the measurement mirror M' need not actually be moved to the null position, once it is known, but rather need only be movable to the various measurement positions.

In accordance with the present invention, at least one frequency shifter FS is positioned in at least one of the arms 18, 20. In the embodiment shown, the frequency shifter FS is positioned in the reference arm 18, but it is to be understood that the frequency shifter FS can be positioned in the measurement arm 20 or that a second frequency shifter (not shown) can be positioned in the measurement arm 20.

As intended by the present invention, the frequency shifter FS shifts the frequency of light propagating through it by an amount Δf to facilitate heterodyne detection of interference fringes caused by the interference of the reference beam with the measurement beam after the beams have been reflected by the object 12. The detection of such fringes indicates that the interferometer optical path difference, discussed above, matches the object optical path difference between the reference and measurement beams within the object 12, discussed more fully below. By "match" is meant that the two optical path differences bear a predetermined proportional relationship to each other, e.g., one to one. Preferably, the precision of the match is on the order of the coherence length of the light source.

In a preferred embodiment, the frequency shifter FS is non-moving. By "non-moving" is meant functionally non-moving, i.e., that the frequency shifter FS preferably does not have to be moved to shift the frequency of light. Thus, the frequency shifter FS can be established by, e.g., an acousto-optic frequency shifter or a phase modulator. It is to be understood, however, that the frequency shifter FS can be established by a moving mirror, a moving cube, a moving glass plate, a moving beam splitter, a moving retroreflector, or a moving lens, provided that the frequency shifter FS can be moved sufficiently quickly to generate a heterodyne beat frequency of at least ten million Hertz (10 MHz), and more preferably a heterodyne beat frequency of at least forty million Hertz (40 MHz).

As shown in FIG. 1, the beams from the interferometer 14 are reflected by the exit beam splitter BS out of the interferometer 14 and along an object path 22, toward the object 12. Both beams are reflected by a strongly reflecting reference surface of the object 12, preferably the anterior surface 24. However, if the anterior surface 24 is insufficiently reflective, a glass plate (not shown) or other highly reflective yet transmissive object can be positioned in front of the object 12 at a fixed distance to it to function as the reference surface.

Additionally, both beams are reflected by measurement sites along the z-axis within the object 12. FIG. 1 shows one such measurement site 26 that is distanced from the reference surface 24 by an object differential distance "z". It is the purpose of the present invention to measure the various object differential distances "z" from the reference surface 24 to the various internally reflective measurement sites 26 of the object 12. Moreover, the present invention not only measures the distances from the reference surface 24 to the various measurement sites 26, but also measures the backscattering potential (i.e., reflectivity) of the various measurement sites 26. All of the reflected beams propagate back through the exit beamsplitter BS' and can be focussed on a receiver, such as a photodetector PD, by a lens L1.

In accordance with present principles, when the interferometer differential distance "d" equals one of the object differential distances "z", the corresponding reflected reference beam from the reference surface 24 and reflected measurement beam from the measurement site 26 will interfere. Owing to the fact that the frequency shifter FS shifted the frequency of one of the beams by an amount Δf, when the beams interfere they generate an optical so-called beat signal characterized by intensity modulations with frequency Δf, which acts as a carrier frequency.

The skilled artisan will appreciate that the beat signal is converted to an electrical signal by the photodetector PD. The signal is then sent to a signal processor SP for demodulation. The demodulation can be undertaken by band pass filtering the signal with a filter centered on Δf and detecting its envelope, the magnitude of which is related to the backscattering potential of the measurement site 26 of interest. Then, the signal is converted to digital format by an analog to digital converter AD, and then stored in a computer PC for correlating the processed signal to a measurement site having depth "z" relative to the reference surface 24 and a backscattering potential as represented by the contrast of the interference fringes, using correlation principles understood in the art. Alternatively, the beat signal can be immediately converted to a digital signal and then processed numerically by a computer or digital signal processor.

Thus, it may now be appreciated that the measurement mirror M' is positioned at various locations to establish various values for the interferometer differential distance "d", with the interference fringes being recorded (or not) at each position as indicative of whether and how strong a backscattering site exists at a distance "z" from the reference surface 24 in the object 12. Since both the reference beam and measurement beam are reflected by the object 12, the apparatus 10 is insensitive to axial motion of the object 12 during measurement.

The backscattering sites at a distance "z" from the reference surface 24 are all in a common "coherence layer" at distance "z". By "coherence layer" is meant that layer within the object sought to be mapped whose distance to the reference point (the point on the object at which the reference beam is reflected) is equal to the interferometer path length difference. Any backscattering structure within the coherence layer will reflect the measurement beam such that it interferes with the reference beam. As understood by the present invention, the position of the coherence layer is determined by the value of the interferometer path difference, and the curvature of the coherence layer is determined by the geometry of the light path.

As described more fully below in reference to FIG. 2, to record the two dimensional backscattering potential distribution within each coherence layer, either the object 12 or the measurement beam can be moved in a raster scan for each interferometer differential distance "d". To avoid aliasing artifacts, the beat frequency Δf should be larger than the frequencies caused by intensity variations during the raster scanning, which can be caused by locally varying areas within the coherence layer. It may now be further understood that the present invention preferably uses a non-moving frequency shifter FS, because such a frequency shifter is better able to produce relatively large beat frequencies Δf than are moving Doppler-type devices.

Now referring to FIG. 2, a particularly preferred embodiment of the present apparatus is shown, generally designated 100, for generating data representative of the three-dimensional distribution of light backscattering sites and their reflectivity in a transparent or semi-transparent object 102, such as a human eye. It is to be understood that the apparatus 100 shown in FIG. 2 is identical in operation and purpose to the apparatus 10 shown in FIG. 1, with the exceptions noted below. Instead of a Michelson interferometer, the apparatus 100 uses a Mach-Zehnder interferometer 104, which establishes a base on which the below-disclosed components are movably or fixedly mounted as set forth herein. As recognized by the present invention, the use of such an interferometer facilitates processing the two beam components independently of each other such that each component can be focussed independently of the other at its own respective depth within the object 102, and such that parallel wave fronts of the return beams can be obtained at the photodetector.

As shown in FIG. 2, the apparatus 100 includes a short coherence, broadband light source LS that directs a beam of light into an entrance path 106 of the interferometer 104. To avoid excessive frequency shifts and/or to avoid the cancellation of frequency shifts, as well as to minimize degradation in signal-to-noise ratio that could otherwise occur if the light beam passed through the frequency shifter FS twice, instead of once, a polarizer P is positioned in the entrance path 106 or other appropriate location between the light source LS and frequency shifter.

Light propagating along the entrance path 106 impinges upon an entrance beamsplitter BS 1, which splits the beam into a reference beam propagating along a reference arm or path 108 and a measurement beam propagating along a measurement arm or path 110.

First considering the reference arm of the interferometer 104, light propagating along the reference arm 108 is reflected by a fixed reference mirror M 1 toward a first polarizing beamsplitter PBS 1. It is to be understood that the polarizing beamsplitters discussed herein are used only when polarized light is used, so that the reference beam traverses the frequency shifter only once; otherwise, the polarizing beamsplitters can be replaced with respective mirrors. In the latter case, the frequency shifter is positioned anywhere in the reference beam, or indeed any where in the measurement beam.

The first polarizing beamsplitter PBS 1 permits light from the reference mirror M 1 to pass therethrough. Owing to the polarization of the light effected by the polarizer P, substantially none of the reference beam from the reference mirror M 1 is reflected by the first polarizing beamsplitter PBS1.

The reference beam continues from the beamsplitter PBS 1 to at least one preferably non-moving frequency shifter FS, where its frequency is shifted in accordance with principles discussed previously. Then, the reference beam may pass through an optionally rotatable half wave plate HWP, which rotates the polarization of the reference beam to its original orientation or other desired orientation. The half wave plate HWP is necessary only if the frequency shifter FS rotates the polarization plane of the frequency shifted beam, such as might occur for certain types of frequency shifters, e.g., AO frequency shifters. As intended by the present invention, once the half wave plate HWP is oriented in the appropriate position it is not necessary to further rotate the half wave plate HWP.

From the half wave plate HWP, the reference beam propagates through a second polarizing beamsplitter PBS 2, it being understood that the second polarizing beamsplitter PBS 2 is configured for permitting substantially all light having the polarization of the reference beam to pass therethrough, without reflecting the light. As stated above, when the frequency shifter is not bypassed in the return direction, the second polarizing beamsplitter PBS 2 can be replaced by a mirror.

To prevent light beams that travel back through the contralateral light path of the interferometer 104 from affecting the data, and to improve the quality of the wave fronts of the reference beams returning from the object 102, a reference spatial filter S 1 is positioned in the reference arm 108. In one preferred embodiment, the reference spatial filter S 1 includes a first reference lens L 5 that focusses light onto an aperture 112 in a reference aperture plate A 1, and a second reference lens L 6 that receives light from the aperture plate and in turn focusses the light onto the reference surface of the object 102 (the vertex of the cornea when the object 102 is a human eye). In the embodiment shown, in which the object 102 is a human eye, the reference surface of the object 102 is an anterior surface 114 of the object 102. As can be appreciated in reference to FIG. 2, reference beams returning from the object 102 are focussed by the second reference lens L 6 onto the aperture 112, and when the return reference beam is diffracted through the aperture 112, it passes through the first reference lens L 5, which refracts the beam to have a plane parallel wave front.

From the reference spatial filter S 1, the reference beam propagates to an exit beamsplitter BS 2, where it is transmissively passed out of the interferometer 104 to an object path 116. When the frequency shifter FS is to be bypassed by returning light beams, a quarter wave plate QWP is positioned in the object path 116 as shown.

From the quarter wave plate QWP, the reference beam propagates to the object 102, where at least a portion of the reference beam is reflected by the reference surface 114 of the object 102 and back along the path just described. Specifically, the reflected reference beam passes through the quarter wave plate QWP, exit beamsplitter BS 2, and back into the reference arm or path 108 of the interferometer 104. As discussed above, the return reference beam is conditioned by the reference spatial filter S 1, and then the return reference beam propagates to the second polarizing beamsplitter PBS 2.

Owing to the polarization of the return beam, the return beam is substantially completely reflected by the second polarizing beamsplitter PBS 2 to a reference path delay unit PDU 1. As shown, the reference path delay unit PDU 1 includes first and second reference delay mirrors M 3, M 2, with the return beam being reflected by the first reference delay mirror M 3 to the second reference delay mirror M 2. In turn, the second reference delay mirror M 2 reflects the beam to the first polarizing beamsplitter PBS1, and then back along the remainder of the reference arm 108 to the entrance beamsplitter BS 1. It may now be appreciated that owing to above-described cooperation of structure, the reference beam passes through the non-moving frequency shifter FS only once.

In accordance with the present invention, the reference path delay unit PDU 1 is translationally movable in the directions indicated by the arrows 118, to establish a reference path length differential distance $d_1$ as shown. Suitable means, such as a small servo, can be used to move the reference path delay unit PDU 1.

From the entrance beamsplitter BS 1, the light passes through an exit lens L 1, which focusses the light onto a photodetector PD for subsequent processing by a signal processor SP, analog to digital converter AD, and computer PC as described above in reference to FIG. 1. Thus, beam components exiting the entrance beamsplitter BS 1 have parallel wave fronts and can be focussed at the photodetector PD, in which case the beams are confocal to their respective conjugate points at or within the object 102. In contrast, beam components propagating back through the contralateral interferometer path will not have parallel wave fronts when they exit the entrance beamsplitter BS 1 and consequently will not pass the confocal aperture that is effectively in front of the photodetector PD. Accordingly, beam components propagating back through the contralateral interferometer path will not be used for the interferometric distance measurements.

Now considering the measurement arm 110, light propagating along the arm 110 from the entrance beamsplitter BS 1 is reflected by a first fixed measurement path mirror M 10 to a measurement path delay unit PDU 2. As shown, the measurement path delay unit PDU 2 includes first and second measurement delay mirrors M 9, M 8, with the beam being reflected by the first measurement delay mirror M 9 to the second measurement delay mirror M 8. In turn, the second measurement delay mirror M 8 reflects the beam to a second fixed measurement path mirror M 7. It is to be understood that designations M 8, M 9 can alternatively be replaced by a retroreflector that can be used in lieu of first and second measurement delay mirrors.

In accordance with the present invention, the measurement path delay unit PDU 2 can be translationally movable in the directions indicated by the arrows 120, to establish a measurement path length differential distance $d_2$ as shown. By providing two path delay units PDU 1, PDU 2, the detection of measurement sites that are close to the reference surface 114 of the object 102 (i.e., that are shallow) is facilitated. Suitable means, such as a small servo, can be used to move the measurement path delay unit PDU 2.

FIG. 2 shows that the light from the second measurement path mirror M 7 propagates to a dispersion compensation element DC. Per the present invention, the dispersion compensation element DC is configured to compensate for the net differences of the group dispersive effects of the optical elements in the two arms 108, 110, and those caused by the different path lengths within the object 102. In so doing, the dispersion compensation element DC improves the axial resolution of the apparatus 100. In one preferred embodiment, the dispersion compensation element DC is established by two wedge-shaped glass plates juxtaposed as shown, with at least one of the wedges being movable in the directions indicated by the arrows δ to establish the distance through which the light must pass through the wedges to thereby compensate for dispersive effects.

While FIG. 2 shows the dispersion compensation element DC positioned in the measurement arm 110, when the group dispersive effect caused by different path lengths within the object 102 is larger than that caused by the additional optical elements in the reference arm 108, the dispersion compensation element DC is positioned in the reference arm 108. Or, a respective dispersion compensation element can be positioned in each arm 108, 110 of the interferometer 104.

A measurement spatial filter S 2 is positioned in the measurement arm 110. The measurement spatial filter S 2 is in all essential respects identical in construction and operation to the reference spatial filter S 1 discussed above. Accordingly, the measurement spatial filter S 2 includes a first measurement lens L 2 that focusses light onto an aperture 122 in a measurement aperture plate A 2, and second measurement lens L 3 that receives light from the aperture plate and in turn directs the light onto a scanning mirror M 4.

As intended by the present invention, the scanning mirror M 4 scans the measurement beam across the particular coherence layer sought to be mapped in the object 102. In the preferred embodiment, the mirror M 4 is tiltably moved about both the x-axis and y-axis in a raster scan, as indicated by the x arrows and y arrows, which are shown orthogonal to each other in FIG. 2. Accordingly, the scanning mirror M 4 is movably mounted on the interferometer 104 by suitable means, e.g., a gimbal, for permitting tiltable motion of the mirror M 4 in two degrees of freedom. Alternatively, two mirrors can be used in lieu of the scanning mirror M 4, each being tiltable in a single degree of freedom. One or more servos can be used to move the scanning mirror M 4.

As shown in FIG. 2, the scanning mirror M 4 reflects the measurement beam to a measurement exit lens L 4. The measurement beam propagates through the lens L 4 to the exit beamsplitter BS 2, and thence onto the object 102. As indicated in FIG. 2, the measurement beam is reflected by a measurement site in the object 102 (e.g., the retina or deeper layers of the ocular fundus when the object 102 is a human eye), and returns via the measurement path or arms 110 just described to the photodetector PD.

As intended by the present invention, the measurement path lenses L 3 and L 4, in cooperation with the refractive elements of the object 102, focus the measurement beam onto the desired measurement site. Refractive errors of the object 102, e.g., a human eye, can be accommodated for using additional measurement path lenses (not shown), or with movable lenses or lenses having variable focal lengths. In any case, the focal length of the measurement exit lens L 4 is established to image the pivot point of the scanning mirror M 4 substantially onto the nodal point of the object 102. Moreover, either or both of the measurement path lenses L 3, L 4 can be translationally moved, e.g., by servos, or have their focal lengths changed, in consonance with varying the interferometer path delay, to focus the beam onto the measurement site sought to be detected.

With further regard to the path delay within the interferometer 104, it may now be understood that when the frequency shifter FS is bypassed in the return direction (i.e., that when the polarizing beamsplitters PBS 1 and PBS 2 are used), the interferometer path difference=$2d_1-4d_2$ (plus differences that are attributable to different optical elements in one path 108, 110 vis-a-vis the other path 110, 108.) Otherwise, (i.e., when the frequency shifter FS is not bypassed in the return direction), the interferometer path difference=$4d_1-4d_2$ (plus differences that are attributable to different optical elements in one path 108, 110 vis-a-vis the other path 110, 108.)

FIG. 3 shows an additional detail of the interferometer 104. Because the transversal distribution of backscattering sites is determined by moving the scanning mirror M 4 to tilt the measurement beam as described above, the coherence layer within the object will be curved. In the case of the human eye, the curvature of the coherence layer can be different from the curvature of the surfaces (e.g., the retina) to be measured, as shown in solid lines in FIG. 3. The present invention recognizes that the light path of the measured beam be established such that the curvature of the coherence layer is about equal to the curvature of structures, e.g., the retina, sought to be imaged.

To accommodate such differences in curvature, a coherence layer correcting element CLC can be positioned between the scanning mirror M 4 and the lens L 4 to alter the optical path length of the tilted measurement beam as a function of the scanning angle, thereby effectively altering the curvature of the coherence layer to match that of the surfaces to be measured as shown in dashed lines in FIG. 3. In the embodiment shown in FIG. 3, the coherence layer correcting element CLC is a glass plate. Alternatively, the coherence layer correcting element can be two glass wedges similar to the dispersion compensation element DC, with the understanding that the wedges can be moved (e.g., by servos or other means) to establish their relative transversal position as appropriate for the scan angle and for the curvature of the measured surface.

Figure 4:
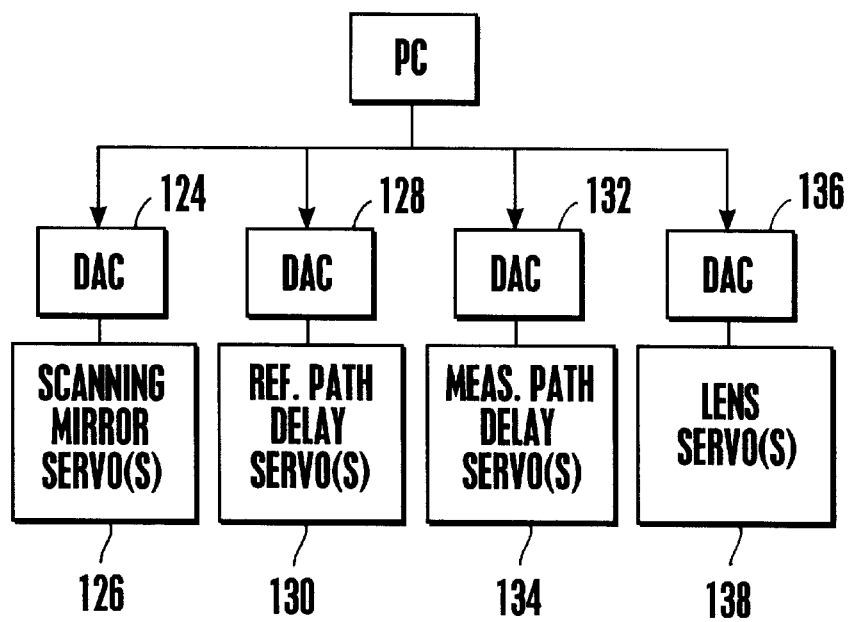
FIG. 4 is a block diagram of the electrical control components.

FIG. 4 shows that the computer PC can control various components within the interferometer 104 in accordance with the principles discussed above. More particularly, the computer PC can send signals to a digital to analog converter (DAC) 124 to control one or more servos 126 for moving the scanning mirror M 4, in accordance with the disclosure above. Also, the computer PC can send signals to a digital to analog converter (DAC) 128 to control one or more servos 130 for translationally moving the reference path delay unit PDU 1, in accordance with the disclosure above. Moreover, the computer PC can send signals to the digital to analog converter (DAC) 132 to control one or more servos 134 for translationally moving the measurement path delay unit PDU 2, in accordance with the disclosure above. Furthermore, the computer PC can send signals to a digital to analog converter (DAC) 136 to control one or more servos 138 for moving one or more of the lenses and/or coherence layer correcting element CLC and/or dispersion compensating element in accordance with the disclosure above.

Figure 5:
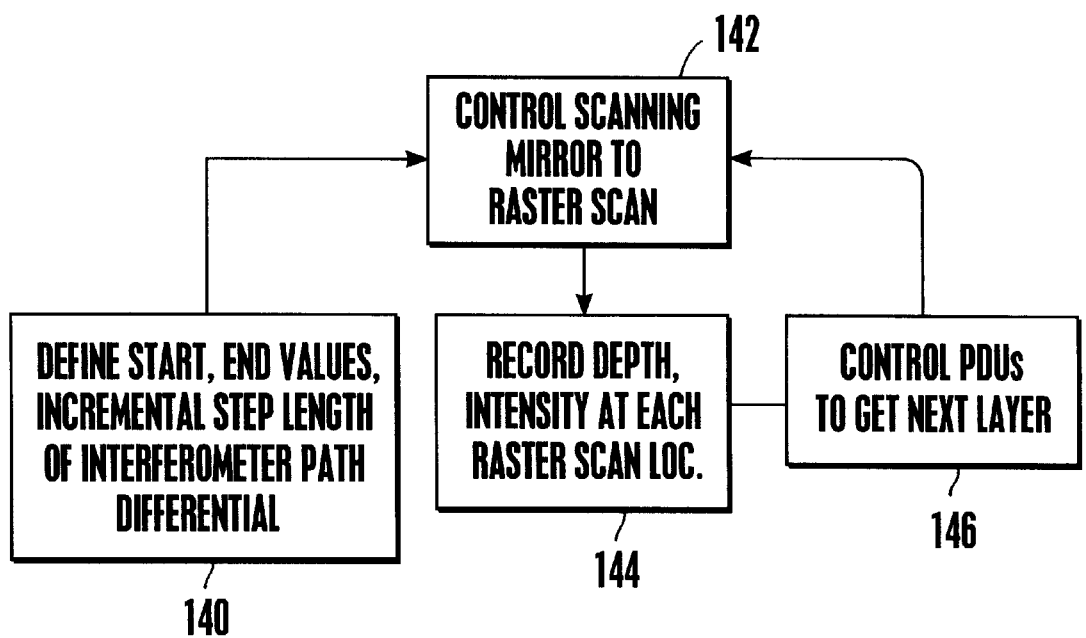
FIG. 5 is a flow chart of the process used by the apparatus to generate a three-dimensional map of an object.

FIG. 5 illustrates the logic undertaken by the computer PC in generating data that is useful for rendering a three-dimensional map of a transparent or semi-transparent object. As set forth below, to generate a three-dimensional map, consecutive coherence layers are sequentially raster scanned, with the distance between coherence layers being about equal to the coherence length of the light source.

Accordingly, commencing at block 140, a start and an end value, as well as an incremental step length of the interferometer path length differential, are defined. Beginning with the start value of the path length differential, the logic undertakes the following steps. The scanning mirror M 4 is controlled, using the scanning mirror servo 126, to move the measurement beam in a raster scan as disclosed. At block 144, at each point in the raster scan the contrast of the interference fringes for the present value of the path length differential is recorded. These values can be correlated to backscattering potential and coherence layer depth, relative to the reference layer of the object, as discussed above. When the raster scan for a coherence layer has been completed, the logic moves to block 146 to increment the interferometer path length differential by the step length by signalling one or both of the PDU servos 130, 134 to move. The logic then loops back to block 142 to raster scan the new coherence layer. These steps are repeated until the end value of the interferometer path length differential is reached.

While the particular METHOD AND APPARATUS FOR RECORDING THREE-DIMENSIONAL DISTRIBUTION OF LIGHT BACKSCATTERING POTENTIAL IN TRANSPARENT AND SEMI-TRANSPARENT STRUCTURES as herein shown and described in detail is fully capable of attaining the above-described objects of the invention, it is to be understood that it is the presently preferred embodiments of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more".

What is claimed is:

1. An apparatus for measuring the distribution profile of a light scattering potential of an object defining a plurality of measurement sites, comprising:

(b) at least one light source generating a plurality of light beams including at least one reference light beam and at least one measurement light beam, the light beams having short coherence length:

(c) at least one frequency shifter positioned in at least one beam path of the light beams;

(d) a receiver receiving reflected light from at least one measurement site and from at least one reference site, the receiver generating a signal representative thereof;

(f) at least one optical scanner positioned to direct at least the measurement light beam to at least one selectable measurement site;

(g) at least one polarizer and one quarter wave plate, wherein the polarizer and the quarter wave plate are positioned in a return beam path such that light in the return beam path returning from the object is directed to avoid passing the frequency shifter, wherein the signal generated by the receiver is usable for determining a multi-dimensional distribution of a light scattering potential of the object.

2. The apparatus claim of 1, wherein the reference site and measurement sites are at selectable locations defined by the object, such that axial motion of the object relative to the light beams equally affects the reference light beam and the measurement light beam.

3. The apparatus of claim 1, further comprising a Michelson interferometer, the interferometer comprising a single beam splitter at which the measurement light beam and the reference light beam overlap.

4. The apparatus of claim 1, further comprising a dispersion compensation element positioned in at least one of the measurement light beam and the reference light beam.

5. The apparatus of claim 1, further comprising at least one movable path delay unit, wherein a focusing lens and the optical scanner direct the measurement light beam in three dimensional space and wherein a profile of the scattering potential of the object is mapped by establishing the focal point of the measurement light beam at plural measurement sites and controlling a path delay between the measurement light beam and the reference light beam using the path delay unit.

6. The apparatus of claim 1, further comprising at least one spatial filter in the measurement light beam or the reference light beam such that the spatial filter is positioned at a focal point conjugate to a focal point of either the reference site, or a measurement site.

7. The apparatus of claim 1, wherein the signal generated at the receiver has a beat frequency when a traveling distance of the reference light beam and a traveling distance of the measurement light beam are substantially matched.

8. An apparatus for measuring the distribution profile of a light scattering potential of an object defining at least one reference site and a plurality of measurement sites, the apparatus comprising:

(b) a plurality of light beams comprising at least one reference light beam and at least one measurement light beam, the light beams having short coherence length;

(c) at least one frequency shifter positioned in at least one beam path of the light beams;

(d) an optics system including at least one focusing lens, the optics system directing the measurement light beam to a measurement site and directing the reference light beam to the reference site, the optics system directing reflected light from a selected measurement site and from the reference site to a receiver generating an output signal;

(e) an optical scanner positioned in at least the measurement light beam and directing the measurement light beam to at least one selectable measurement site; and (f) at least two beam splitters, the measurement light beam and the reference light beam substantially overlapping at the beam splitters.

9. The apparatus claim of 8, wherein the optics system comprises at least one measurement beam focusing lens in a measurement beam path and at least one reference beam focusing lens in a reference beam path, such that the reference site and the measurement site are selectable at different focal planes.

10. The apparatus of claim 8, further comprising a dispersion compensation element positioned in at least one of the measurement light beam and the reference light beam.

11. The apparatus of claim 8, further comprising at least one movable path delay unit, wherein a focusing lens and the optical scanner direct the measurement light beam in three dimensional space and wherein a profile of the scattering potential of the object is mapped by establishing the focal point of the measurement light beam at plural measurement sites and controlling a path delay between the measurement light beam and the reference light beam using the path delay unit.

12. The apparatus of claim 8, further comprising at least one spatial filter in the measurement light beam or the reference light beam such that the spatial filter is positioned at a focal point conjugate to a focal point of either the reference site, or a measurement site.

13. The apparatus of claim 8, wherein the signal generated at the receiver has a beat frequency when a traveling distance of the reference light beam and a traveling distance of the measurement light beam are substantially matched.

14. An apparatus for measuring the distribution profile of a light scattering potential of a fundus layers of the eye, comprising:

(a) a light source generating a plurality of light beams including at least one reference light beam and at least one measurement light beam;

(b) at least one frequency shifter positioned in at least one beam path of the light beams;

(c) a plurality of optics directing the measurement light beam to a measurement site and the reference light beam to the reference site, the optics further directing reflected light from a selected measurement site and from the reference site to a receiver generating an ouput signal;

(d) at least one optical scanner positioned in at least the measurement light beam to direct the measurement light beam to at least one selectable measurement site; and (e) at least one beam path compensator element in the measurement light beam, such that a coherence layer from which the signal is derived has a curvature which is substantially matched with a curvature of the fundus layers when the measurement light beam is scanned by the optical scanner.

15. The apparatus of claim 14, wherein the beam path compensator element is selected from the group including: a glass plate with plane parallel surfaces, and a pair of movable wedges forming plane parallel surfaces with adjustable optical thickness.

16. The apparatus of claim 14, further comprising at least one movable path delay unit, wherein a focusing lens and the optical scanner direct the measurement light beam in three dimensional space and wherein a profile of the scattering potential of the eye is mapped by establishing the focal point of the measurement light beam at plural measurement sites and controlling a path delay between the measurement light beam and the reference light beam using the path delay unit.

17. The apparatus of claim 14, further comprising at least one spatial filter in the measurement light beam or the reference light beam such that the spatial filter is positioned at a focal point conjugate to a focal point of either the reference site, or a measurement site.

18. The apparatus of claim 14, wherein the signal generated at the receiver has a beat frequency when a traveling distance of the reference light beam and a traveling distance of the measurement light beam are substantially matched.

19. The apparatus of claim 14, further comprising a dispersion compensation element positioned in at least one of the measurement light beam and the reference light beam.

20. A method for measuring the distribution profile of light scattering potential of an object, comprising:

(a) generating light beams with short coherence length;

(b) scanning at least one of the light beams in at least one dimension with at least one optical scanner;

(c) shifting the optical frequency of at least one of the light beams with a non-moving frequency shifter;

(d) directing the light beams toward the object with an optics system including a first focusing lens in the measurement light beam such that the measurement light beam forms a focal point at a measuring site, and a second focusing lens in the reference light beam such that the reference light beam forms a focal point at a reference site, the measurement site and the reference site being selectable at different focal planes defined by the object;

(e) directing reflected light beams from the object to a receiver;

(f) controlling at least one path delay unit such that a travel distance of the measurement light beam and a travel distance of the reference light beam are substantially matched; and (g) generating a signal using the receiver, the signal having a beat frequency defined at least in part by the controlling act, whereby axial motion of the object relative to an incident direction of the light beams with respect to the object equally affects the reference light beam and the measurement light beam.

21. The method of claim 20, wherein the path delay unit comprises at least one translationally movable mirror or retroreflector to selectively establish the length of one arm of travel for at least one of: the measurement light beam, or the reference light beam.

22. The method of claim 20, further comprising moving the focusing lens in the measurement light beam such that a profile of the scattering potential can be mapped by positioning the focal point of the measurement light beam and controlling the path delay unit to selected locations defined by the object.

23. The method of claim 20, further comprising inserting at least one dispersion compensator element in at least one of the measurement light beam or the reference light beam.

24. The method of claim 20, further comprising inserting at least one spatial filter in the measurement light beam or in the reference light beam such that the spatial filter is positioned at a focal point conjugate to the focal point of either the reference site or a measurement site.

25. The method of claim 20, wherein the path delay unit comprises at least one translationally movable mirror or retroreflector to selectively establish the length of one arm of travel for at least one of: the measurement light beam, or the reference light beam.

26. A method of measuring the distribution profile of light scattering potential of an object, comprising:
(a) generating light beams with short coherence length;
(b) scanning at least one of the light beams in at least one dimension with at least one optical scanner;
(c) shifting the optical frequency of at least one of the light beams with a non-moving frequency shifter;
(d) directing the light beams toward the object with a plurality of optics;
(e) controlling at least one path delay unit such that the travel distance of the measurement light beam and the travel distance of the reference light beam are matched;
(f) generating a signal defining a beat frequency established at least in part by the controlling act; and
(f) inserting a polarizer and a quarter wave plate in a light beam path including the frequency shifter, such that at least the measurement light beam is directed to avoid passing the frequency shifter in its return from the object.

27. The method of claim 26, wherein the path delay unit comprises at least one translationally movable mirror or retroreflector to selectively establish the length of one arm of travel for at least one of: the measurement light beam, or the reference light beam.

28. The method of claim 26, further comprising moving the focusing lens in the measurement light beam such that a profile of the scattering potential can be mapped by positioning the focal point of the measurement light beam and controlling the path delay unit to selected locations defined by the object.

29. The method of claim 26, further comprising inserting at least one dispersion compensator element in at least one of the measurement light beam or the reference light beam.

30. The method of claim 26, further comprising inserting at least one spatial filter in the measurement light beam or in the reference light beam such that the spatial filter is positioned at a focal point conjugate to the focal point of either a reference site or a measurement site.

31. A method of measuring the distribution profile of light scattering potential of an object, comprising:
(a) generating light beams with short coherence length;
(b) scanning at least one of the light beams in at least one dimension with at least one optical scanner;
(c) shifting the optical frequency of at least one of the light beams with a non-moving frequency shifter;
(d) directing the light beams towards the object with a plurality of optics comprising a first focusing lens in the measurement light beam such that the measurement light beam forms a focal point at a measurement site, and a second focusing lens in the reference light beam such that the reference light beam forms a focal point at a reference site, the measurement site and the reference site being selected at different focal planes defined by the object;
(e) controlling at least one path delay unit such that a travel distance of the measurement light beam and a travel distance of the reference light beam are matched;
(f) generating a signal defining a beat frequency established at least in part by the controlling act; and
(g) directing the measurement light beam and the reference light beam to substantially overlap each other at at least two beam splitters in incident and reflected propagation directions relative to the object.

32. The method of claim 31, wherein the path delay unit comprises at least one translationally movable mirror or retroreflector to selectively establish the length of one arm of travel for at least one of: the measurement light beam, or the reference light beam.

33. The method of claim 31, further comprising moving the focusing lens in the measurement light beam such that a profile of the scattering potential can be mapped by positioning the focal point of the measurement light beam and controlling the path delay unit to selected locations defined by the object.

34. The method of claim 31, further comprising inserting at least one dispersion compensator element in at least one of the measurement light beam or the reference light beam.

35. The method of claim 31, further comprising inserting at least one spatial filter in the measurement light beam or in the reference light beam such that the spatial filter is positioned at a focal point conjugate to the focal point of either the reference site or a measurement site.

36. A method of measuring the distribution profile of light scattering potential of a fundus layers of the eye, comprising:
(a) generating light beams with short coherence length;
(b) scanning at least one of the light beams in at least one dimension with at least one optical scanner;
(c) shifting the optical frequency of at least one of the light beams with a non-moving frequency shifter;
(d) directing the light beams towards the eye using a plurality of optics;
(e) controlling at least one path delay unit such that a travel distance of the measurement light beam and a travel distance of the reference light beam are matched;
(f) generating a signal defining a beat frequency established at least in part by the controlling act; and
(g) inserting at least one path compensator element in the measurement light beam path such that a coherence layer from which the signal is derived has a curvature that substantially matches the curvature of the fundus layers of the eye when the measurement light beam is scanned by the optical scanner.

37. The method of claim 36, wherein the path compensator element is selected from the group including: a glass plate with plane parallel surfaces, and a pair of movable wedges forming plane parallel surfaces with adjustable optical thickness.

38. The method of claim 36, further comprising moving a focusing lens in the measurement light beam such that a profile of the scattering potential can be mapped by positioning the focal point of the measurement light beam and controlling the path delay unit to selected locations defined by the object.

39. The method of claim 36, further comprising inserting at least one dispersion compensator element in at least one of the measurement light beam or the reference light beam.

40. The method of claim 36, further comprising inserting at least one spatial filter in the measurement light beam or in the reference light beam such that the spatial filter is positioned at a focal point conjugate to the focal point of either the reference site or a measurement site.

* * * * *